United States Patent [19]
Au-Young et al.

[11] Patent Number: 5,869,637
[45] Date of Patent: Feb. 9, 1999

[54] HUMAN KALLIKREIN

[75] Inventors: Janice Au-Young, Berkeley; Olga Bandman, Mountain; Scott Michael Braxton, San Mateo; Surya K. Goli, Sunnyvale, all of Calif.

[73] Assignee: Incyte Pharmaceuticals, Inc., Palo Alto, Calif.

[21] Appl. No.: 681,151

[22] Filed: Jul. 22, 1996

[51] Int. Cl.$^6$ .......................... C07H 21/02; C07H 21/04; C12N 15/12; C12N 15/63

[52] U.S. Cl. .................... 536/23.5; 536/23.2; 435/320.1; 435/325; 435/252.3; 435/254.11; 935/4; 935/11; 935/22; 935/66

[58] Field of Search .................................. 536/23.2, 23.5; 435/320.1, 325, 252.3, 254.11; 935/4, 11, 22, 66

[56] References Cited

PUBLICATIONS

MacDonald, R., et al., "Molecular biology of tissue kallikrein," *Biochem J.*, 253:313–321 (1988).

Murray, S., et al., "Kallikrein Multigene Families and the Regulation of Their Expression," *Journal of Cardiovascular Pharmacology*, 15(6):S7–S16 (1990).

Schacter, M., "Kallikreins (kininogenases)—a group of serine proteases with bioregulatory actions," *Pharmacol Rev.*, 31:1–17 (1989).

Berry, T., et. al., "A gene for high urinary kallikrein may protect against hypertension in Utah kindreds," *Hypertension*, 13:3–8 (1989).

Woodley–Miller, C., et al., "Restriction fragment length polymorphisms mapped in spontaneously hypertensive rats using kallikrein probes," *J. Hypertens*, 7:865–871 (1989).

Pravenec, M., et al., "Cosegregation of blood pressure with a kallikrein gene family polymorphism," *Hypertension*, 17:242–246 (1991).

Wang, J. et al., "Human tissue kallikrein induces hypotension in transgenic mice," *Hypertension*, 23:236–243 (1994).

Griffin, J., et al., Mechanisms for the involvement of high molecular weight kiniogen in surface–dependent reactions of Hageman factor, *Proc. Natl. Acad. Sci. USA*, 73:2554–2558 (1976).

Heimark, R., et al., "Surface activation of blood coagulation, fibrinolysius and kinin formation," *Nature*, 286:456–460 (1980).

Schapira, M., et al., "Purified human plasma kallikrein aggregates human blood neutrophils," *J. Clin. Invest.*, 69:1199–1202 (1982).

Wiggins, R., et al., "Chemotactic activity genereated from the fifth component of complement by plasma kallikrein of the rabbit," *J. Exp. Med.*, 153:1391–1404 (1981).

Clements, J., et al., "Glandular kallikrein gene expression in the human uterus," *Brazilian J. Med. Biol. Res.*, 27:1855–1863 (1994).

Seidah, N., et al., "Mouse Plasma kallikrein: cDNA structure, enzyme characterization, and comparison of protein and mRNA levels among species," *DNA and Cell Biology*, 9(10):737–748 (1990) (GI 205011).

Wines, D., et al., "Evolution of the Rat Kallikrein Gene Family: Gene Conversion Leads to Functional Diversity," *J. Mol. Evol.*, 32:476–492 (1991).

Nolly, H., et al., "A Local Kallikrein–kinin system is present in rat hearts," *Hypertension*, 23:919–923 (1994).

Wachtfogel, Y., et al., "Selective kallikrein inhibitors alter human neutrophil elastase release during extracorporeal circulation," *Am. J. Physiol*, 268:H1352–H1357 (1995).

Szelke, M. et al., "Synthetic inhibitors of tissue kallikrein: effects in vivo in a model of allergic inflammation," *Braz. J. Med. Biol. Res.*, 27:1943–1947 (1994).

Dela Cadena, R., et al., "Inhibition of plasma kallikrein prevents peptidoglycan–induced arthritis in the Lewis rat," *FASEB J.*, 9:446–452 (1995).

Wang, C., et al., "Direct gene delivery of human tissue kallikrein reduces blood pressure in spontaneously hypertensive rats," *J. Clin. Invest.*, 95:1710–1716 (1995).

Seidah, N., et al., "The cDNA structure of rat plasma kallikrein," *DNA*, 8:563–574 (1989) (GI 205011).

Baker, A., et al., "Human kidney kallikrein: cDNA cloning and sequence analysis," *DNA*, 4:445–450 (1985) (GI 125170).

Hillier, L et al., (GI 1716421) GenBank Sequence Database (Accession AA147031), National Center for Biotechnology Information, National Library of Medicine, Bethesda, Maryland, 20894, submitted Dec. 14, 1996.

Pisano, "Kinins in Nature" from Bradykinin, Kallidin and Kallikrein, supplement Ed. E.G. Erdas, Springer–Verlag, 1979, pp. 273–285.

*Primary Examiner*—Ronald B. Schwadron
*Attorney, Agent, or Firm*—Sheela Mohan-Peterson; Lucy J. Billings; Incyte Pharmaceuticals, Inc.

[57] ABSTRACT

The present provides a polynucleotide which identifies and encodes a novel human kallikrein (HKLP). The invention provides for genetically engineered expression vectors and host cells comprising the nucleic acid sequence encoding HKLP. The invention also provides for the use of substantially purified HKLP and its agonists, antagonists, or inhibitors in the commercial production of recombinant proteins and in pharmaceutical compositions for the treatment of diseases associated with the expression of HKLP. Additionally, the invention provides for the use of antisense molecules to HKLP in pharmaceutical compositions for treatment of diseases associated with the expression of HKLP. The invention also describes diagnostic assays which utilize diagnostic compositions comprising the polynucleotide, fragments or the complement thereof, which hybridize with the genomic sequence or the transcript of polynucleotides encoding HKLP or anti-HKLP antibodies which specifically bind to HKLP.

5 Claims, 11 Drawing Sheets

```
                  9          18          27    36         45         54
5' CAT CAG CTG GGA GTC TTC TCT TTT CCC TGC ACT TGT TCA AAC CAA CTG TTA TAA 63          72          81    90         99        108
   ATA CCT CAT CAT GTT CTT TTC TTG CAC CAT TTT GGT ACC AAA ATG TGA TGT GAA TAC 117         126         135   144        153        162
   AGG CGA GCG TAT CCC TCC TTG CAG ATT GGC CAT TTT GGT TGA ACA CTC TAA AGA ACG CTG 171         180         189   198        207        216
   TGA GTC TGT TCT TGG GAT TGT GGG CCT ACA GCC TGA AGA CAC AGA TTG CAG 225         234         243   252        261        270
   TCA ATT TCC AGA GGA AAA TTC AGA CAA TCA AAC CTG CCT GAT GCC TGA TGA ATA 279         288         297   306        315        324
   TGT GGA AGA ATG CTC ACC TAG TCA TTT CAA GTG CCG CTC AGG ACA GTG TGT TCT 333         342         351   360        369        378
   GGC TTC CAG AAG ATG TGA TGG CCA GGC CGA CTG TGA CGA TGA CAG TGA TGA GGA 387         396         405   414        423        432
   AAA CTG TGG TTG TAA AGA GAG AGA TCT TTG GGA ATG TCC ATC CAA TAA ACA ATG 441         450         459   468        477        486
   TTT GAA GCA CAC AGT GAT CTG CGA TGG GTT CCC AGA CTG CCC TGA TTA CAT GGA
```

```
495              504              513              522              531              540
CGA GAA AAA CTG CTC ATT TTG CCA AGA TGA TGA GCT GGA ATG TGC AAA CCA TGC 549              558              567              576              585              594
GTG TGT GTC ACG TGA CCT GTG GTG TGA TGG TGA AGC CGA CTG CTC AGA CAG TTC 603              612              621              630              639              648
AGA TGA ATG GGA CTG TGT GAC CTC TCT ATA AAT GTG AAC TCC TCT TCC TTT CTG
         M   G   L   C   D   L   S   I   N   V   N   S   S   F   L 657              666              675              684              693              702
ATG CAC AGA GCT GCC ACA GAA CAC CAT GTG TGT GCA GAT GGC TGG CAG GAG
 M   V   H   R   A   A   T   E   H   H   V   C   A   D   G   W   Q   E 711              720              729              738              747              756
ATA TTG AGT CAG CTG GCC TGC AAG CAG ATG GGT TTA GGA GAA CCA TCT GTG ACC
 I   L   S   Q   L   A   C   K   Q   M   G   L   G   E   P   S   V   T 765              774              783              792              801              810
AAA TTG ATA CAG GAA CAG GAG AAA GAG CCG CGG TGG CTG ACA TTA CAC TCC AAC
 K   L   I   Q   E   Q   E   K   E   P   R   W   L   T   L   H   S   N 819              828              837              846              855              864
TGG GAG AGC CTC AAT GGG ACC ACT TTA CAT GAA CTT CTA GTA AAT GGG CAG TCT
 W   E   S   L   N   G   T   T   L   H   E   L   L   V   N   G   Q   S
```

```
       873            882            891            900            909            918
TGT GAG AGC AGA AGT ATT TCT CTT CTG TGT ACT AAA CAA GAC TGT GGG CRC
 C   E   S   R   S   I   S   L   L   C   T   K   Q   D   C   G   X 927            936            945            954            963            972
CGC CCT GCT GCC CGA ATG AAC AAA AGG ATC CTT GGA GGT CGG AGT CGC CCT
 R   P   A   A   R   M   N   K   R   I   L   G   G   R   S   R   P 981            990            999           1008           1017           1026
GGA AGG TGG CCA TGG CAG TGT TCT CTG CAG AGT GAA CCC AGT GGA CAT ATC TGT
 G   R   W   P   W   Q   C   S   L   Q   S   E   P   S   G   H   I   C 1035           1044           1053           1062           1071           1080
GGC TGT GTC CTC ATT GCC AAG AAG TGG GTT CTG ACA GTT GCC CAC TGC TTC GAG
 G   C   V   L   I   A   K   K   W   V   L   T   V   A   H   C   F   E 1089           1098           1107           1116           1125           1134
GGG AGA GAG AAT GCT GCA GTT YGG AAA GTG GTG CTT GGC ATC AAC AAT CTA GAC
 G   R   E   N   A   A   V   X   K   V   V   L   G   I   N   N   L   D 1143           1152           1161           1170           1179           1188
CAT CCA TCA GTG TTC ATG CAG ACA CGC TTT GTG AAG ACC ATC ATC CTG CAT CCC
 H   P   S   V   F   M   Q   T   R   F   V   K   T   I   I   L   H   P 1197           1206           1215           1224           1233           1242
CGC TAC AGT CGA GCA GTG GTG GAC TAT GAC ATC AGC ATC GTT GAG CTG AGT GAA
 R   Y   S   R   A   V   V   D   Y   D   I   S   I   V   E   L   S   E
```

FIGURE 1C

```
     1251           1260           1269           1278           1287           1296
GAC ATC AGT GAG ACT GGC TAC GTC CGG CCT GTC TGC TTG CCC AAC CCG GAG CAG
 D   I   S   E   T   G   Y   V   R   P   V   C   L   P   N   P   E   Q 1305           1314           1323           1332           1341           1350
TGG CTA GAG CCT GAC ACG TAC TGC TAT ATC ACA GGC TGG GGC CAC ATG GGC AAT
 W   L   E   P   D   T   Y   C   Y   I   T   G   W   G   H   M   G   N 1359           1368           1377           1386           1395           1404
AAA ATG CCA TTT AAG CTG CAA GAG GGA GAG GTC CGC ATT ATT TCT CTG GAA CAT
 K   M   P   F   K   L   Q   E   G   E   V   R   I   I   S   L   E   H 1413           1422           1431           1440           1449           1458
TGT CAG TCC TAC TTT GAC ATG AAG ACC ATC ACT CGG ATG ATA TGT GCT GGC
 C   Q   S   Y   F   D   M   K   T   I   T   R   M   I   C   A   G 1467           1476           1485           1494           1503           1512
TAT GAG TCT GGC ACA GTT GAT TCA TGC ATG GGT GAC AGC GGT GGG CCT CTT GTT
 Y   E   S   G   T   V   D   S   C   M   G   D   S   G   G   P   L   V 1521           1530           1539           1548           1557           1566
TGT GAG AAG CCT GGA GGA CGG TGG ACA TTA TTT GGA TTA ACT TCA TGG GGC TCC
 C   E   K   P   G   G   R   W   T   L   F   G   L   T   S   W   G   S 1575           1584           1593           1602           1611           1620
GTC TGC TTT TCC AAA GTC CTG GGG CCT GGC GTT TAT AGT AAT GTG TCA TAT TTC
 V   C   F   S   K   V   L   G   P   G   V   Y   S   N   V   S   Y   F
```

FIGURE 1D

```
    1629            1638            1647            1656            1665            1674
GTC GAA TGG ATT AAA AGA CAG ATT TAC ATC CAG ACC TTT CTC CTA AAC TAA TTA
 V   E   W   I   K   R   Q   I   Y   I   Q   T   F   L   L   N 1683            1692            1701            1710            1719            1728
TAA GGA TGA TCA GAG ACT TTT GCC AGT ACA CTA AAA GAA ATG GCC TTC TTG ACT

1737
GTG AGA GCT G 3'
```

FIGURE 1E

```
The Electronic Northern for Clone: 307474
and Stringency = 50

Library    Lib Description                              Abun    Pct Abun
-------    ---------------                              ----    --------
HEARNOT01  heart, 56 M                                    1       0.071

The Northern Link Info returned a total of 1 results.
```

```
  1  - - M G L - - - - - - - - - - F K Q V G Y F V S L F A T V S C G C L S Q L Y A N T F F R G G D L A A I Y - - - - - - -   SEQ ID NO1
  1  - - M I L - - - - - - - - - - - - - - - - - - - - - - - - - - - - - - - - - - - - - - - - - - - - - - - - - - - - -   SEQ ID NO3
  1  - - M - - - - - - - - - - - - - - - - - W F L V L - - - - - - - - - - - - - - - - - - - - - - - - - - - - - - - - -   SEQ ID NO4

4  - - - - - - - - - - - - - - - - - - - - - - - - - - - - - - - - - - - - - - - - - - - - - - - - - - - - F L M - - -   SEQ ID NO1
 41  T P D A Q H C Q K M C T F H P R C L L F S F L A V S P T K E T D K R F G C F M K - -                                   SEQ ID NO3
  7  - - - C D - - - - - - - - - - - - - - C L A L S L - L S I N V N S S S - - - - - - - - -                               SEQ ID NO4

18  - - - - - - - - - - - - - - - V H R A A T E - - - - - - - - - - - - - - - - - - - - - - - - - - - Q L D - - -       SEQ ID NO1
 81  E S I T G T L P R I H R T G A I S G H S L K Q C G H Q L S A C H Q D I Y E G L D - -                                   SEQ ID NO3
 13  - G G T G A A P P I Q S - - - - - - - - - - - - - - - - - - - - - - - - - - - - -                                   SEQ ID NO4

25  - - - - - - - - - - - - - - - - - - - - - - - - - - - - - - - - - H H V C A D G - - - - - - - - - W Q - -             SEQ ID NO1
121  M R G S N F N I S K T D S I E E C Q K L C T N N I H C Q F F T Y A T K A F H R P                                       SEQ ID NO3
 24  - - - - - - - - - - - - - - - - - - - - - - - - - - - - - - - - - - - - - - - - -                                   SEQ ID NO4

34  - E I - - - - - - - - - - - - - - - - - - - - - - - - - - - - - - I K P V D N L V S G F S L K S C A L S E I G         SEQ ID NO1
161  E Y R K S C L L K R S S G T P T S I K P V D N L V S G F - -                                                           SEQ ID NO3
 24  - - - - - - - - - - - - - - - - - - - - - - R I V G G - -                                                             SEQ ID NO4

41  - C - - - - K Q M G L G E P S V T K L I Q E Q E K E P R W L - T L H S N - - - - - -                                   SEQ ID NO1
201  C P M D I F Q H F A F A D L N V S Q V V T P D A F V C R T V C T F H P N C L F F - -                                   SEQ ID NO3
 29  - - - - - - - - - - - - - - - - - - - - - - - - - - - - W E C E Q H S Q                                               SEQ ID NO4
```

```
198 YSRAVVDY--DISIVELSEDISE-TGYVRPVCLPNPEQWL   SEQ ID NO1
475 YKMSEGSY--DIALIKLQTPLNY-TEFQKPICLPSKADTN   SEQ ID NO3
110 TRQADEDYSHDLMLLRLTEPADTITDAVKVVELPTQEP--   SEQ ID NO4

235 EPDTYCYITGWGHMG-NKMPFK--LQEGEVRIISLEHCQS   SEQ ID NO1
512 TIYTNCWVTGWGYTK-ERGETQNILQKATIPLVPNEECQK   SEQ ID NO3
148 EVGSTCLASGWGSIEPENFSEPDDLQCVDLKILPNDECEK   SEQ ID NO4

272 YFDMKTITTRMICAGYESGTVDSCMGDSGGPLVCEKPGGR   SEQ ID NO1
551 KYRDYVITKQMICAGYKEGGIDACKGDSGGPLVC-KHSGR   SEQ ID NO3
188 A-HVQKVTDFMLCVGHLEGGKDTCVGDSGGPLMCDGV--   SEQ ID NO4

312 WTLFGLTSWGSVCFSKVLGPGVYSNVSYFVEWI--KRQIY   SEQ ID NO1
590 WQLVGITSWGEGC-ARKEQPGVYTKVAEYIDWILEKIQSS   SEQ ID NO3
224 --LQGVTSWGYVPCGTPNKPSVAVRVLSYVKWIEDTI--   SEQ ID NO4

350 IQTFLLN                                   SEQ ID NO1
629 KERALETSPA                                SEQ ID NO3
259 ----AENS                                  SEQ ID NO4
```

FIGURE 3C

HUMAN KALLIKREIN

FIELD OF THE INVENTION

The present invention relates to nucleic acid and amino acid sequences of a novel human kallikrein and to the use of these sequences in the diagnosis, study, prevention and treatment of disease.

BACKGROUND OF THE INVENTION

Kallikreins are a large family of homologous serine proteases that act in a variety of circulatory and immune system functions (MacDonald R J et al (1988) Biochem J 253: 313–321; Murray S R et al (1990) J Cardiovasc Pharmacol 15 Suppl 6: S7–16). They may exist in blood plasma or be associated with the cell membrane. Kallikreins act both locally and systemically to regulate blood flow and pressure. They are capable of specifically cleaving low molecular weight kininogen to generate vasoactive kinin peptides, such as the potent vasodialator, bradykinin (Pisano J J (1979) Handb Exp Pharmacol 25: suppl 273–285; Schachter M (1979) Pharmacol Rev 31: 1–17). Genetic and transgenic studies have also indicated that kallikreins play a role in blood pressure regulation (Berry T D et al (1989) Hypertension 13: 3–8; Woodley-Miller et al 1989; Pravenac M et al (1991) Hypertension 17: 242–246; Wang J et al (1994) Hypertension 23: 236–243).

Kallikrein has a dual function in the blood coagulation cascade. Kallikrein can promote blood clot formation by activating factor XI, an early component of the cascade (Griffin J H et al (1976) Proc Natl Acad Sci 73: 2554–2558) and in an existing blood clot can stimulate the formation of plasmin, which will lyse the clot and destroy clotting factors (Heimark R L et al (1980) Nature 286: 456–460).

Kallikrein has important immunological functions. Plasma kallikrein can stimulate human neutrophils to aggregate and degranulate, releasing their lysosomal contents (Schapira M et al (1982) J Clin Invest 69: 1199–1202). In addition, plasma kallikrein incubated with the complement component C5 generates immunologically active fragments of C5 (Wiggins R C et al (1981) J Exp Med 153: 1391–1404). Several investigators have found evidence for a kallikrein role in the inflammatory response. In one study, Clements J A et al (1995, Endocrinology 136: 1137–1144) reported tissue kallikrein expression and activity in the periovalatory period in the gonadotropin-primed immature female ovary suggesting a role in the inflammatory-like response at ovulation.

The greatest nucleotide differences among the kallikreins are in the 5' end of the mRNA. The regulation of the mRNA stability and/or turnover rate of kallikrein may be affected by its 5' end in a species-dependent manner (Seidah N G et al (1990) DNA Cell Biol 9: 737–748). In addition, researchers speculate that small sequence differences among kallikrein genes play a role in generating diverse patterns of tissue-specific expression and function (Wines D R et al (1991) J Mol Evol 32: 476–492).

A local kallikrein-kinin system is present in rat hearts (Nolly N et al (1994) Hypertension 23: 919–923). Evidence was found for kallikrein activity and gene expression in rat heart tissues. Kinins mediate part of the beneficial cardiac effects induced by treatment with angiotensin-converting enzyme inhibitors in ischemia-reperfusion injury, myocardial infarction, and cardiac hypertrophy. Researchers did not determine whether the rat heart kallikrein-kinin system acts independently of the kallikrein-kinin systems of other tissues or blood plasma.

Kallikreins and Disease

Cardiopulmonary bypass can cause severe hemorrhagic complications by initiating a biochemical and cellular inflammatory response. It has been suggested that selective inhibitors of kallikrein may be effective in the attenuation of the contact-mediated inflammatory response in cardiopulmonary bypass (Wachtfogel Y T et al (1995) Am J Physiol 268: H1352–1357).

The selective tissue kallikrein inhibitor CH-694 caused highly significant decrease in kallikrein activity and in airway resistance when administered intraperitoneally before or after challenge in ovalbumin-sensitized guinea pigs (Szelke M et al (1994) Braz J Med Biol Res 27: 1943–1947). Thus, inhibitors of tissue kallikrein may prove effective in the treatment of allergic inflammation.

Specific kallikrein inhibitors decrease joint swelling and anemia in a rat model for arthritis, perhaps by interfering with kallikrein induced inflammatory reactions (Dela Cadena R A et al (1995) FASEB J 9: 446–452). Thus, specific kallikrein inhibitors may have therapeutic potential for arthritis patients.

The potential for using kallikrein gene therapy for the treatment of high blood pressure was investigated in rats. Human kallikrein gene delivered intravenously to spontaneously hypertensive rats caused a significant and sustained reduction in systemic blood pressure (Wang C et al (1995) J Clin Invest 95: 1710–1716). Therefore, kallikrein gene therapy may one day become a treatment option for the approximately 25% of the population afflicted with hypertension.

Angiotensin-converting enzyme inhibitors (ACEi) are widely used in the treatment of hypertension and heart failure. Evidence suggests that kinins mediate some of the effects of ACEi in treatments for ischemia-reperfusion injury, myocardial infarction, and cardiac hypertrophy (Nolly et al, supra). Involvement of kinins in the cardiac effects of ACEi suggests the presence of an independent cardiac kallikrein-kinin system. Whereas, 14 kallikrein gene family members have been characterized in mice, only 3 have been discovered to date in humans, none of which are localized to the heart (Wines et al, supra). Discovery of a kallikrein active in the heart is very desirable, as it provides the possibility of new treatments for hypertension, heart failure, inflammation, and blood clotting disorders.

SUMMARY

The present invention discloses a novel human kallikrein (hereinafter referred to as HKLP), characterized as having homology to rat kallikrein (GI 205011) and human kidney kallikrein. Accordingly, the invention features a substantially purified kallikrein, as shown in amino acid sequence of SEQ ID NO:1, and having characteristics of the kallikrein protease family.

One aspect of the invention features isolated and substantially purified polynucleotides which encode HKLP. In a particular aspect, the polynucleotide is the nucleotide sequence of SEQ ID NO:2. In addition, the invention features polynucleotide sequences that hybridize under stringent conditions to SEQ ID NO:2.

The invention further relates to nucleic acid sequence encoding HKLP, oligonucleotides, peptide nucleic acids (PNA), fragments, portions or antisense molecules thereof. The present invention also relates to an expression vector which includes polynucleotide encoding HKLP and its use to transform host cells or organisms.

BRIEF DESCRIPTION OF THE FIGURES

FIGS. 1A, 1B, 1C show the amino acid sequence (SEQ ID NO:1) and nucleic acid sequence (SEQ ID NO:2) of the novel kallikrein, HKLP produced using MACDNASIS software (Hitachi Software Engineering Co Ltd).

FIG. 2 shows the northern analysis for Incyte Clone 307474 (SEQ ID NO:2) produced electronically using LIFESEQ® database (Incyte Pharmaceuticals, Palo Alto Calif.). The percentage abundance is calculated by multiplying the number of transcripts found in the library times 100 and dividing the product by the total number of transcripts in the library.

FIGS. 3A and 3B shows the amino acid sequence alignments among HKLP (SEQ ID NO:1), rat kallikrein (GI 205011; SEQ ID NO:3), and human kidney kallikrein (GI 125170; SEQ ID NO:4) produced using the multisequence alignment program of DNASTAR software (DNAStar Inc, Madison Wis.).

DETAILED DESCRIPTION OF THE INVENTION

Figure 4:
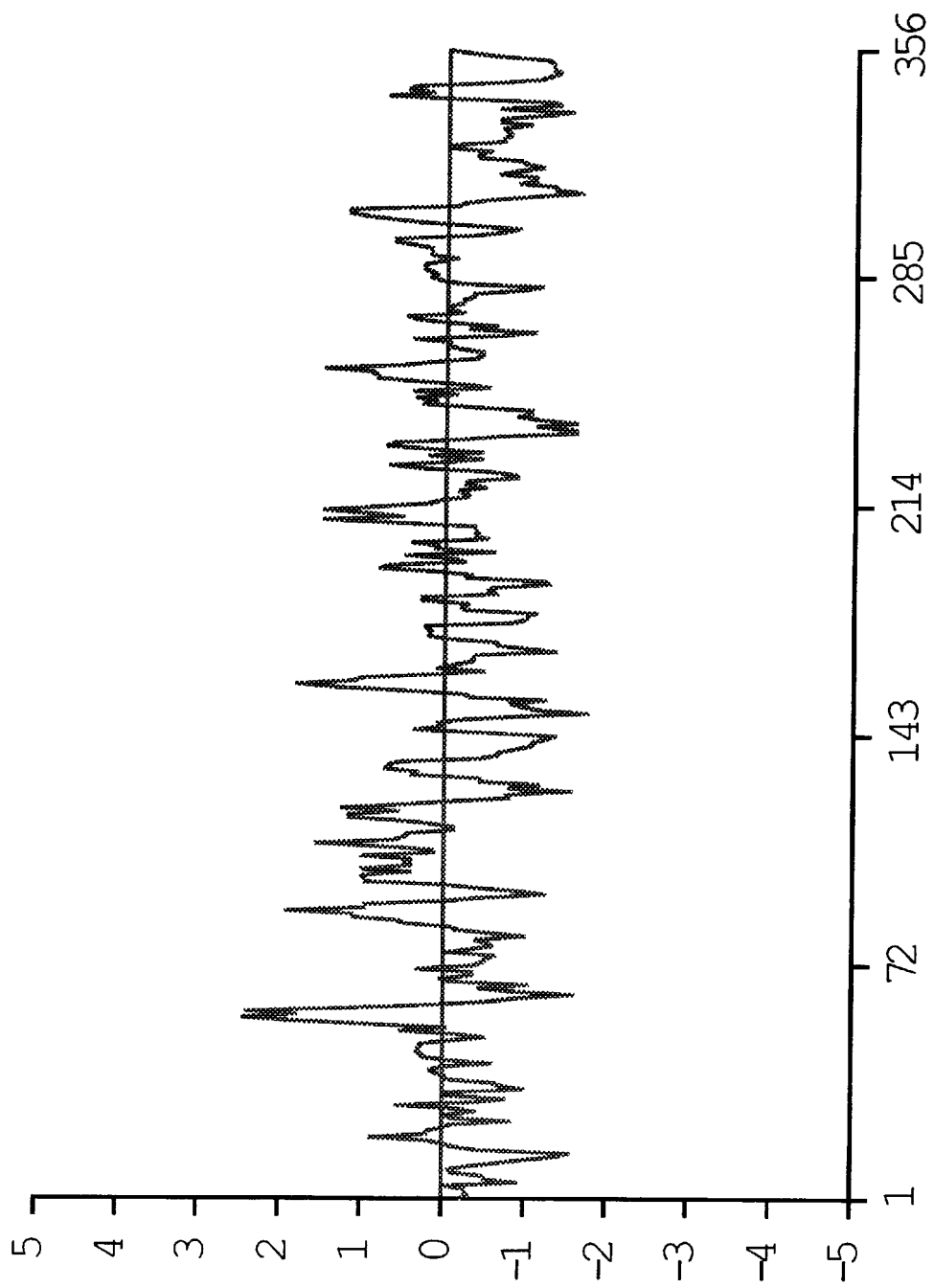
FIG. 4 shows the hydrophobicity plot (generated using MACDNASIS software) for HKLP, SEQ ID NO:1; the X axis reflects amino acid position, and the negative Y axis, hydrophobicity (FIGS. 4 and 5).

Definitions "Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, HKLP refers to the amino acid sequence of substantially purified HKLP obtained from any species, particularly mammalian, including bovine, ovine, porcine, murine, equine, and preferably human, from any source whether natural, synthetic, semi-synthetic or recombinant.

A "variant" of HKLP is defined as an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to a HKLP having structural, regulatory or biochemical functions of the naturally occurring HKLP. Likewise, "immunologically active" defines the capability of the natural, recombinant or synthetic HKLP, or any oligopeptide thereof, to induce a specific immune response in appropriate animals or cells and to bind with specific antibodies.

The term "derivative" as used herein refers to the chemical modification of a nucleic acid encoding HKLP or the encoded HKLP. Illustrative of such modifications would be replacement of hydrogen by an alkyl, acyl, or amino group.

A nucleic acid derivative would encode a polypeptide which retains essential biological characteristics of natural HKLP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm−5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HKLP.

A "substitution" results from the replacement of one or more nucleotides or amino acids by different nucleotides or amino acids, respectively.

Description

The present invention relates to a novel human kallikrein initially identified among the cDNAs from a heart tissue library (HEARNOT01) and to the use of the nucleic acid and amino acid sequences in the study, diagnosis, prevention and treatment of disease. cDNAs encoding a portion of UBCP were only found in a heart tissue-derived library (FIG. 2).

The present invention also encompasses HKLP variants. A preferred HKLP variant is one having at least 80% amino acid sequence similarity to the HKLP amino acid sequence (SEQ ID NO:1), a more preferred HKLP variant is one having at least 90% amino acid sequence similarity to SEQ ID NO:1 and a most preferred HKLP variant is one having at least 95% amino acid sequence similarity to SEQ ID NO:1.

Figure 3B:
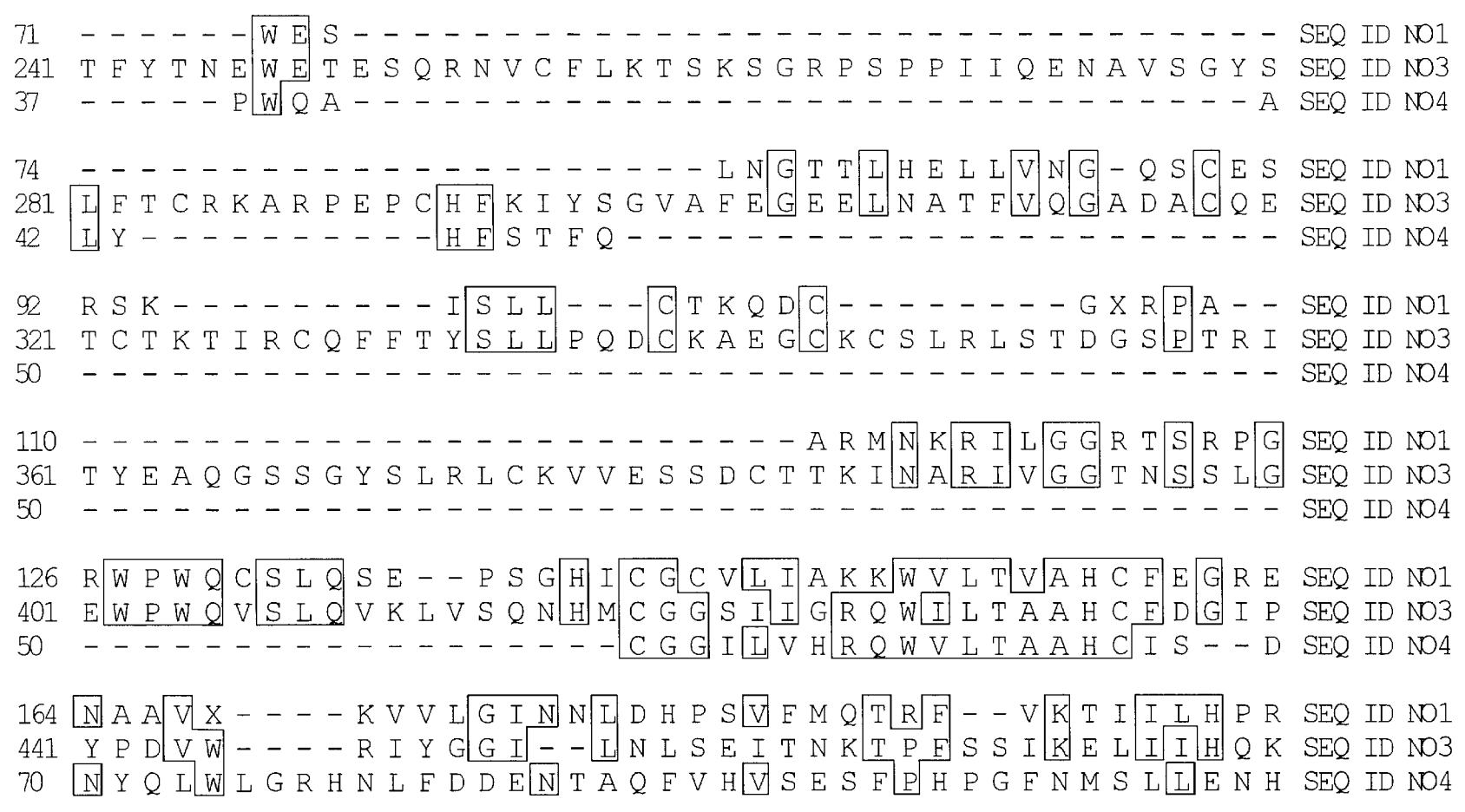

Nucleic acid encoding the human kallikrein of the present invention was first identified in cDNA, Incyte Clone 307474 (SEQ ID NO:2), through a computer-generated search for amino acid sequence alignments. The HKLP nucleic acid sequence, SEQ ID NO:2; encodes the HKLP amino acid sequence, SEQ ID NO:1. The present invention is based, in part, on the chemical and structural homology among HKLP, rat kallikrein (GI 205011; Seidah N G et al, (1989) DNA 8: 563–574, and human kidney kallikrein (GI 125170; Baker A R et al (1985) DNA 4: 445–450; FIGS. 3A and 3B). HKLP has 35% identity to rat kallikrein and 33% identity to human kidney kallikrein. Analysis of the hydrophobicity plots indicate that both HKLP and rat kallikrein share hydrophobicity in the amino terminus suggesting a signal sequence that directs the molecules to a membrane. Unlike the rat kallikrein, a plasma kallikrein, HKLP is hydrophobic in the carboxy terminus and thus likely to remain membrane bound. The novel HKLP is 356 amino acids long and has three potential glycosylation sites.

The HKLP Coding Sequences

The nucleic acid and deduced amino acid sequences of HKLP are shown in FIGS. 1A, 1B, and 1C. In accordance with the invention, any nucleic acid sequence which encodes the amino acid sequence of HKLP can be used to generate recombinant molecules which express HKLP. In a specific embodiment described herein, a partial sequence of the nucleic acid encoding HKLP was first isolated as Incyte Clone 307474 from a heart tissue cDNA library (HEARNOT01).

It will be appreciated by those skilled in the art that as a result of the degeneracy of the genetic code, a multitude of HKLP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring HKLP, and all such variations are to be considered as being specifically disclosed.

Although nucleotide sequences which encode HKLP and its variants are preferably capable of hybridizing to the nucleotide sequence of the naturally occurring HKLP under appropriately selected conditions of stringency, it may be advantageous to produce nucleotide sequences encoding HKLP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HKLP and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a HKLP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a gene encoding HKLP.

Also included within the scope of the present invention are polynucleotide sequences that are capable of hybridizing to the nucleotide sequence of FIGS. 1A, 1B, and 1C under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology,* Vol 152, Academic Press, San Diego Calif.) incorporated herein by reference.

Altered nucleic acid sequences encoding HKLP which may be used in accordance with the invention include deletions, insertions or substitutions of different nucleotides resulting in a polynucleotide that encodes the same or a functionally equivalent HKLP. The protein may also show deletions, insertions or substitutions of amino acid residues which produce a silent change and result in a functionally equivalent HKLP. Deliberate amino acid substitutions may be made on the basis of similarity in polarity, charge, solubility, hydrophobicity, hydrophilicity, and/or the amphipathic nature of the residues as long as the biological activity of HKLP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of HKLP. As used herein, an "allele" or "allelic sequence" is an alternative form of HKLP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE (US Biochemical Corp, Cleveland Ohio)), TAQ polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton MICROLAB 2200 (Hamilton, Reno Nev.), Peltier Thermal Cycler (PTC200; M J Research, Watertown Mass.) and the ABI 377 DNA sequencers (Perkin Elmer).

Extending the Polynucleotide Sequence

The polynucleotide sequence of the gene encoding HKLP may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J D et al (1991; Nucleic Acids Res 19:3055–60). Additionally, one can use PCR, nested primers and PROMOTERFINDER libraries to walk in genomic DNA (PROMOTERFINDER) Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode HKLP, fragments of the polypeptide, fusion proteins or functional equivalents thereof may be used in recombinant DNA molecules that direct the expression of HKLP in appropriate host cells. Due to the inherent degeneracy of the genetic code, other DNA sequences which encode substantially the same or a functionally equivalent amino acid sequence, may be used to clone and express HKLP. As will be understood by those of skill in the art, it may be advantageous to produce HKLP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HKLP expression or to produce recombinant RNA transcripts having desirable properties, such as a longer half-life, than transcripts produced from naturally occurring sequence.

The nucleotide sequences of the present invention can be engineered in order to alter a HKLP coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant sequence encoding HKLP may be ligated to a heterologous sequence to encode a fusion protein. For example, screening of peptide libraries for inhibitors of HKLP activity, it may be useful to encode a chimeric HKLP protein that is recognized by a commercially available antibody. A fusion protein may also be engineered to contain a cleavage site located between a HKLP sequence and the heterologous protein sequence, so that the HKLP may be cleaved and purified away from the heterologous moiety.

In an alternate embodiment of the invention, the coding sequence of HKLP may be synthesized, whole or in part, using chemical methods well known in the art (see Caruthers M H et al (1980) Nuc Acids Res Symp Ser 215–23, Horn T et al (1980) Nuc Acids Res Symp Ser 225–32, etc). Alternatively, the protein itself could be produced using chemical methods to synthesize a HKLP amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially by preparative high performance liquid chromatography (eg, Creighton (1983) *Proteins, Structures and Molecular Principles,* W H Freeman and Co, New York N.Y.). The composition of the synthetic peptides may be confirmed by amino acid analysis or sequencing (eg, the Edman degradation procedure; Creighton, supra). Additionally the amino acid sequence of HKLP, or any part thereof, may be altered during direct synthesis and/or combined using chemical methods with sequences from other proteins, or any part thereof, to produce a variant polypeptide.

Expression Systems

In order to express a biologically active HKLP, the nucleotide sequence encoding HKLP or its functional equivalent, is inserted into an appropriate expression vector, ie, a vector which contains the necessary elements for the transcription and translation of the inserted coding sequence.

Methods which are well known to those skilled in the art can be used to construct expression vectors containing a HKLP coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual,* Cold Spring Harbor Press, Plainview N.Y. and Ausubel F M et al (1989) *Current Protocols in Molecular Biology,* John Wiley & Sons, New York N.Y.

A variety of expression vector/host systems may be utilized to contain and express a HKLP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla Calif.) or PSPORT1

(Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of HKLP, vectors based on SV40 or EBV may be used with an appropriate selectable marker.

In bacterial systems, a number of expression vectors may be selected depending upon the use intended for HKLP. For example, when large quantities of HKLP are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the HKLP coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HKLP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology,* Academic Press, New York N.Y., pp 421–463.

An alternative expression system which could be used to express HKLP is an insect system. In one such system, *Autographa californica* nuclear polyhedrosis virus (AcNPV) is used as a vector to express foreign genes in *Spodoptera frugiperda* cells or in *Trichoplusia* larvae. The HKLP coding sequence may be cloned into a nonessential region of the virus, such as the polyhedrin gene, and placed under control of the polyhedrin promoter. Successful insertion of HKLP will render the polyhedrin gene inactive and produce recombinant virus lacking coat protein coat. The recombinant viruses are then used to infect *S. frugiperda* cells or *Trichoplusia* larvae in which HKLP is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a HKLP coding sequence may be ligated into an adenovirus transcription/translation complex consisting of the late promoter and tripartite leader sequence. Insertion in a nonessential E1 or E3 region of the viral genome will result in a viable virus capable of expressing HKLP in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a HKLP sequence. These signals include the ATG initiation codon and adjacent sequences. In cases where HKLP, its initiation codon and upstream sequences are inserted into the appropriate expression vector, no additional translational control signals may be ;needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HKLP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the HKLP is inserted within a marker gene sequence, recombinant cells containing HKLP can be identified by the absence of marker gene function. Alternatively, a marker gene can be placed in tandem with a HKLP sequence under the control of a single promoter. Expression of the marker gene in response to induction or selection usually indicates expression of the tandem HKLP as well.

Alternatively, host cells which contain the coding sequence for HKLP and express HKLP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding HKLP can be detected by DNA-DNA or DNA-RNA hybridization or amplification using probes, portions or fragments of polynucleotides encoding HKLP. Nucleic acid amplification based assays involve the use of oligonucleotides or oligomers based on the sequence encoding HKLP to detect transformants containing DNA or RNA which encoding HKLP or a fragment thereof. As used herein, "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of HKLP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HKLP is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to polynucleotides encoding HKLP include oligolabeling, nick translation, end-labeling or PCR amplification using a labeled nucleotide. Alternatively, the HKLP sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of HKLP

Host cells transformed with a nucleotide sequence encoding HKLP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding HKLP can be designed with signal sequences which direct secretion of HKLP through a prokaryotic or eukaryotic cell membrane. Other recombinant constructions may join HKLP to nucleotide sequence encoding a polypeptide domain which will facilitate purification of soluble proteins (Kroll D J et al (1993) DNA Cell Biol 12:441–53; cf discussion of vectors infra containing fusion proteins).

HKLP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and HKLP is useful to facilitate purification. One such expression vector provides for expression of a fusion protein compromising an HKLP and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying HKLP from the fusion protein.

In addition to recombinant production, fragments of HKLP may be produced by direct peptide synthesis using solid-phase techniques (cf Stewart et al (1969) *Solid-Phase Peptide Synthesis*, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of HKLP may be chemically synthesized separately and combined using chemical methods to produce the full length molecule.

Uses of HKLP

The rationale for use of the nucleotide and polypeptide sequences disclosed herein is based in part on the chemical and structural homology among the novel human HKLP disclosed herein, the rat kallikrein (GI 205011; Seidah et al, supra), and human kidney kallikrein (GI 125170; Baker et al, supra).

Accordingly, HKLP may act in inflammatory pathways, therefore specific inhibitors of HKLP may help prevent inflammation caused by cardiopulmonary bypass, asthma, or other sources. Specific HKLP inhibitors may have therapeutic potential for arthritis patients. Gene therapy using polynucleotides encoding HKLP may be used to treat hypertension in human patients. Alternatively, the delivery of the protein HKLP, in suitable form, may yield sustained reduction in systemic blood pressure. By generating kinins HKLP may provide new treatments for hypertension, stroke, and heart failure.

In those conditions where one wants to decrease kallikrein activity, cells may be transfected with antisense sequences to a gene encoding HKLP or provided with inhibitors of HKLP. Such conditions include hypotension, clotting disorders, and inflammatory diseases.

HKLP Antibodies

HKLP-specific antibodies are useful for the diagnosis of conditions and diseases associated with expression of HKLP. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

HKLP for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of HKLP amino acids may be fused with those of another protein such as keyhole limpet hemocyanin and antibody produced against the chimeric molecule. Procedures well known in the art can be used for the production of antibodies to HKLP.

For the production of antibodies, various hosts including goats, rabbits, rats, mice, etc may be immunized by injection with HKLP or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HKLP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy,* Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HKLP-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HKLP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HKLP and its specific antibody and the measurement of complex formation. A two-site, monoclonal-based immunoassay utilizing monoclonal antibodies reactive to two noninterfering epitopes on a specific HKLP protein is preferred, but a competitive binding assay may also be employed. These assays are described in Maddox DE et al (1983, J Exp Med 158:1211).

Diagnostic Assays Using HKLP Specific Antibodies

Particular HKLP antibodies are useful for the diagnosis of conditions or diseases characterized by expression of HKLP or in assays to monitor patients being treated with HKLP, agonists or inhibitors. Diagnostic assays for HKLP include methods utilizing the antibody and a label to detect HKLP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HKLP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HKLP is preferred, but a competitive binding assay may be employed. These assays are described, among other places, in Maddox, DE et al (1983, J Exp Med 158:1211).

In order to provide a basis for diagnosis, normal or standard values for HKLP expression must be established.

This is accomplished by combining body fluids or cell extracts taken from normal subjects, either animal or human, with antibody to HKLP under conditions suitable for complex formation which are well known in the art. The amount of standard complex formation may be quantified by comparing various artificial membranes containing known quantities of HKLP with both control and disease samples from biopsied tissues. Then, standard values obtained from normal samples may be compared with values obtained from samples from subjects potentially affected by disease. Deviation between standard and subject values establishes the presence of disease state.

Drug Screening

HKLP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HKLP and the agent being tested, may be measured.

Another technique for drug screening which may be used provides for high throughput screening of compounds having suitable binding affinity to the HKLP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HKLP and washed. Bound HKLP is then detected by methods well known in the art. Purified HKLP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HKLP specifically compete with a test compound for binding HKLP. In this manner, the antibodies can be used to detect the presence of any peptide which shares one or more antigenic determinants with HKLP.

Uses of the Polynucleotide Encoding HKLP

A polynucleotide encoding HKLP, or any part thereof, may be used for diagnostic and/or therapeutic purposes. For diagnostic purposes, polynuleotides encoding HKLP of this invention may be used to detect and quantitate gene expression in biopsied tissues in which expression of HKLP may be implicated. The diagnostic assay is useful to distinguish between absence, presence, and excess expression of HKLP and to monitor regulation of HKLP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding HKLP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding HKLP, alleles or related sequences.

Probes may also be used for the detection of related sequences and should preferably contain at least 50% of the nucleotides from any of these HKLP encoding sequences. The hybridization probes of the subject invention may be derived from the nucleotide sequence of SEQ ID NO:2 or from genomic sequence including promoter, enhancer elements and introns of the naturally occurring HKLP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding HKLP include the cloning of nucleic acid sequences encoding HKLP or HKLP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding HKLP may be used for the diagnosis of conditions or diseases with which the expression of HKLP is associated. For example, polynucleotide sequences encoding HKLP may be used in hybridization or PCR assays of fluids or tissues from biopsies to detect HKLP expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The nucleotide sequences encoding HKLP disclosed herein provide the basis for assays that detect activation or induction associated with muscle wasting. The nucleotide sequence encoding HKLP may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding HKLP in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HKLP expression must be established. This is accomplished by combining body fluids or cell extracts taken from normal subjects, either animal or human, with HKLP, or a portion thereof, under conditions suitable for hybridization or amplification. Standard hybridization may be quantified by comparing the values obtained for normal subjects with a dilution series of HKLP run in the same experiment where a known amount of a substantially purified HKLP is used. Standard values obtained from normal samples may be compared with values obtained from samples from patients afflicted with HKLP-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in US Patent Nos. 4,683,195 and 4,965,188, provides additional uses for oligonucleotides based upon the HKLP sequence. Such oligomers are generally chemically synthesized, but they may be generated enzymatically or produced from a recombinant source. Oligomers generally comprise two nucleotide sequences, one with sense orientation (5'->3') and one with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of a relatively high amount of HKLP in extracts of biopsied tissues may indicate the onset of muscle wasting. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to genes encoding kallikreins and its expression profile, polynucleotide sequences encoding HKLP disclosed herein may be useful in the treatment of conditions such as hypertension, cardiac hypertrophy, arthritis, inflammatory disorders, and blot clotting disorders.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding HKLP. See, for example, the techniques described in Sambrook et al (supra) and Ausubel et al (supra).

The polynucleotides comprising full length cDNA sequence and/or its regulatory elements enable researchers to use sequences encoding HKLP as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HKLP can be turned off by transfecting a cell or tissue with expression vectors which express high levels of a desired HKLP-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding HKLP, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding HKLP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HKLP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for HKLP disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for HKLP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques,* Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding HKLP on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example a sequence tagged site based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HKLP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that HKLP or an HKLP derivative can be delivered in a suitable formulation to direct the degradation of specific proteins. Such treatment could lessen systemic blood pressure in patients with hypertension. Similarly, administration of HKLP antagonists may also inhibit the activity or shorten the lifespan of this protein and decrease inflammation caused by various agents.

The examples below are provided to illustrate the subject invention and are not included for the purpose of limiting the invention.

EXAMPLES

I DNA Library Construction

The heart tissue for the heart cDNA library construction was obtained from a 56 year-old Caucasian male (Lot No. HAL194, International Institute for the Advancement of Medicine (IIAM), Exton Pa.). The left ventricle tissue for the left ventricle cDNA library was obtained from a 51 year-old Caucasian female (Lot No. RU95-03-196, IIAM). The right and left atrium tissues for the right and left atrium cDNA libraries, respectively, were obtained from the same Caucasian female.

Each tissue was individually flash frozen, ground in a mortar and pestle. Tissue was lysed immediately in buffer containing guanidinium isothiocyanate and spun through cesium chloride. The precipitate was treated by several phenol chloroform extractions and ethanol precipitation at pH 8. The resulting sample was then DNAsed. The polyadenylated mRNA was then isolated and purified using OIAGEN OLIGOTEX (Qiagen Inc., Chatsworth Calif.)

First strand cDNA synthesis was accomplished using an oligo d(T) primer/linker which also contained an XhoI restriction site. Second strand synthesis was performed using a combination of DNA polymerase I, *E. coli* ligase and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LAMBDA ZAP vector system (Stratagene); then the vector which contained the PBLUESCRIPT phagemid (Stratagene) was transformed into *E. coli* host cells strain XL1-BLUEMRF (Stratagene).

The phagemid forms of individual cDNA clones were obtained by the in vivo excision process. Enzymes from both PBLUESCRIPT and a cotransformed f1 helper phage nicked the DNA, initiated new DNA synthesis, and created the smaller, single-stranded circular phagemid molecules which contained the cDNA insert. The phagemid DNA was released, purified, and used to reinfect fresh host cells (SOLR, Stratagene). Presence of the phagemid which contained the gene for β-lactamase allowed transformed bacteria to grow on medium containing ampicillin.

II Isolation and Sequencing of cDNA Clones

Plasmid DNA was released from the cells and purified using the Miniprep Kit (Catalogue #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog # 22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS™ DNA Purification System (Catalogue #A7100, Promega, Madison Wis.) or QIAWELL 8 Plasmid, QIAWELL PLUS DNA and QIAWELL ULTRA DNA Purification Systems (QIAGEN® Chatsworth Calif.).

The cDNAs were sequenced by the method of Sanger F and A R Coulson (1975; J Mol Biol 94:441f), using a Hamilton MICRO LAB 2200 (Hamilton, Reno Nev.) in combination with four Peltier Thermal Cyclers (PTC200 from M J Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul SF 1993 and 1990, supra) are used to search for identical or related molecules in nucleotide databases such as GenBank or the LIFESEQ® database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of HKLP sequences to Full Length or to Recover Regulatory Elements

The nucleic acid sequence encoding full length HKLP (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known HKLP-encoding sequence "outward" generating amplicons containing new, unknown nucleotide sequence for the region of interest (U.S. patent application Ser. No. 08/487,112, filed Jun. 7, 1995, now abandoned, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M J Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2xCarb. The following day, several colonies are randomly picked from each plate and cultured in 150 µl of liquid LB/2xCarb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with SEPHADEX G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS, Schleicher & Schuell, Durham N.H.). Hybridization is carried out for 16 hours at 40° C. To remove nonspecific signals, blots are sequentially washed at room temperature under increasingly stringent conditions up to 0.1 x saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The HKLP-encoding sequence, or any part thereof, is used to inhibit in vivo or in vitro expression of naturally occurring HKLP. Although use of antisense oligonucleotides, comprising about 20 base-pairs, is specifically described, essentially the same procedure is used with larger cDNA fragments. An oligonucleotide based on the coding sequence of HKLP, as shown in FIGS. 1A, 1B, and 1C, is used to inhibit expression of naturally occurring HKLP. The complementary oligonucleotide is designed from the most unique 5' sequence as shown in FIGS. 1A, 1B, and 1C and used either to inhibit transcription by preventing promoter binding to the upstream nontranslated sequence or translation of an HKLP-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B, 1C.

VIII Expression of HKLP

Expression of the HKLP is accomplished by subcloning the cDNAs into appropriate vectors and transfecting the vectors into host cells. In this case, the cloning vector, pSport, previously used for the generation of the cDNA library is used to express HKLP in *E. coli*. Upstream of the cloning site, this vector contains a promoter for B-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HKLP-encoding polynucleotides. The signal sequence directs the secretion of HKLP into the bacterial growth media which can be used directly in the following assay for activity.

IX HKLP Activity

HKLP activity can be measured by a method described by Nooly et al (1994, supra). HKLP can be incubated with partially purified dog kininogen for 5 hours at 37° C. in the presence of 0.1 mol/L TRIS-HCl buffer (pH 8.5) containing a cocktail of peptidase inhibitors. Generated kinins can be then measured by radioimmunoassay.

X Production of HKLP Specific Antibodies

Figure 5:
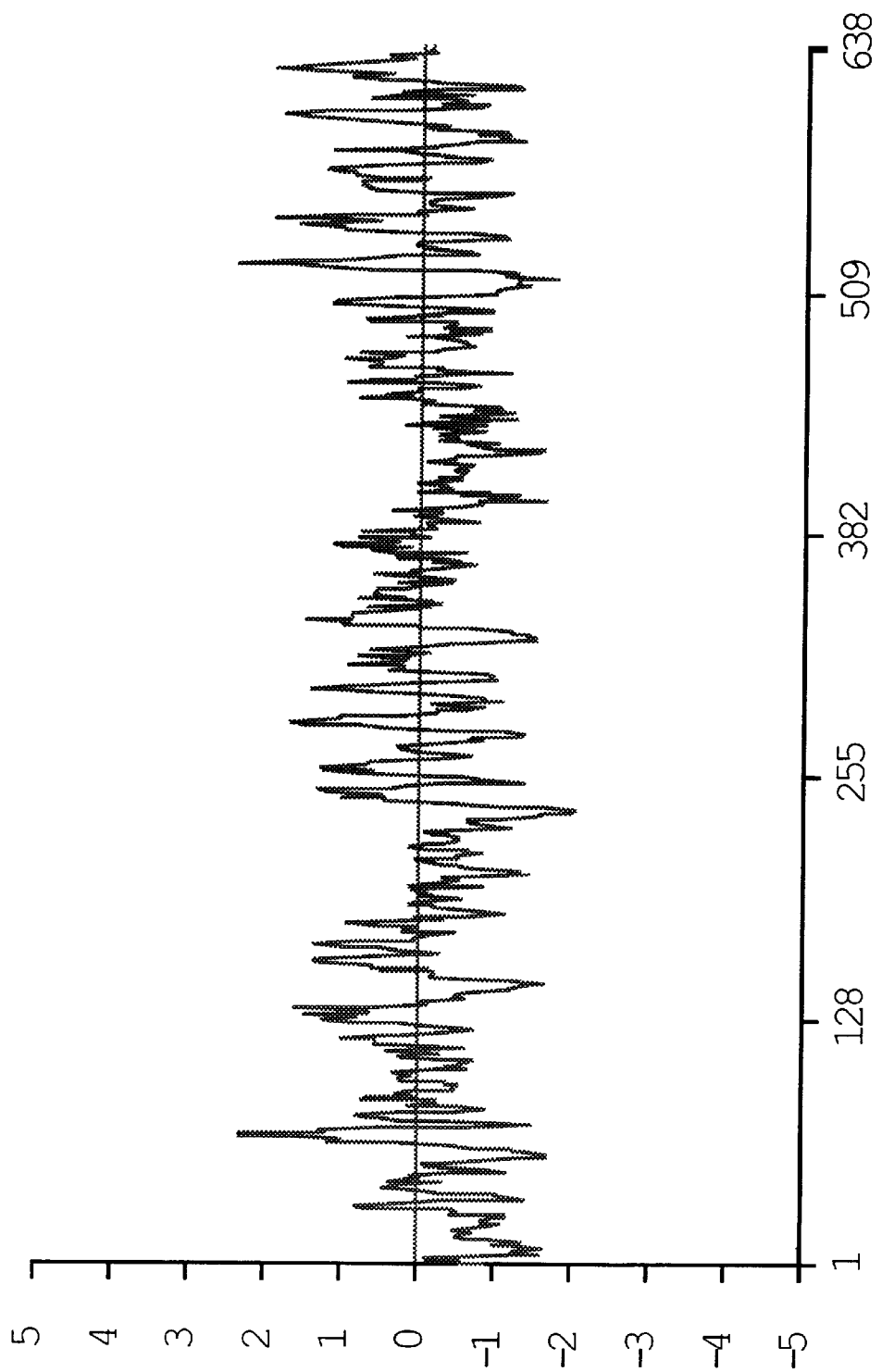
FIG. 5 shows the hydrophobicity plot for rat kallikrein, SEQ ID NO:3.

HKLP substantially purified using PAGE electrophoresis (Sambrook, supra) is used to immunize rabbits and to produce antibodies using standard protocols. The amino acid sequence translated from HKLP is analyzed using DNAS-TAR software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 4 and 5) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HKLP Using Specific Antibodies

Naturally occurring or recombinant HKLP is substantially purified by immunoaffinity chromatography using antibodies specific for HKLP. An immunoaffinity column is constructed by covalently coupling HKLP antibody to an activated chromatographic resin such as CnBr-activated SEPHAROSE (Pharmacia Biotech). After the coupling, the resin is blocked and washed according to the manufacturer's instructions.

Media containing HKLP is passed over the immunoaffinity column, and the column is washed under conditions that allow the preferential absorbance of HKLP (eg, high ionic strength buffers in the presence of detergent). The column is eluted under conditions that disrupt antibody/HKLP binding (eg, a buffer of pH 2–3 or a high concentration of a chaotrope such as urea or thiocyanate ion), and HKLP is collected.

XII Identification of Molecules Which Interact with HKLP

HKLP, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled HKLP, washed and any wells with labelled HKLP complex are assayed. Data obtained using different concentrations of HKLP are used to calculate values for the number, affinity, and association of HKLP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide sequence encoding a polypeptide comprising the amino acid sequence of SEQ ID NO: 1.

2. An isolated and purified polynucleotide sequence of claim 1 consisting of the sequence of SEQ ID NO:2.

3. An isolated and purified polynucleotide sequence fully complementary to the polynucleotide sequence of claim 2.

4. An expression vector containing the polynucleotide sequence of claim 1.

5. A host cell containing the expression vector of claim 4.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 356 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY:HEARNOT01
        ( B ) CLONE: 307474

( x i ) SEQUENCE DESCRIPTION: SEQ ID NO:1:

```
Met  Gly  Leu  Cys  Asp  Leu  Ser  Ile  Asn  Val  Asn  Ser  Ser  Ser  Phe  Leu
 1              5                        10                       15

Met  Val  His  Arg  Ala  Ala  Thr  Glu  His  Val  Cys  Ala  Asp  Gly  Trp
               20                   25                    30

Gln  Glu  Ile  Leu  Ser  Gln  Leu  Ala  Cys  Lys  Gln  Met  Gly  Leu  Gly  Glu
          35                        40                         45

Pro  Ser  Val  Thr  Lys  Leu  Ile  Gln  Glu  Gln  Glu  Lys  Glu  Pro  Arg  Trp
     50                        55                        60

Leu  Thr  Leu  His  Ser  Asn  Trp  Glu  Ser  Leu  Asn  Gly  Thr  Thr  Leu  His
 65                  70                        75                             80

Glu  Leu  Leu  Val  Asn  Gly  Gln  Ser  Cys  Glu  Ser  Arg  Ser  Lys  Ile  Ser
                85                        90                        95

Leu  Leu  Cys  Thr  Lys  Gln  Asp  Cys  Gly  Xaa  Arg  Pro  Ala  Ala  Arg  Met
               100                      105                      110

Asn  Lys  Arg  Ile  Leu  Gly  Gly  Arg  Thr  Ser  Arg  Pro  Gly  Arg  Trp  Pro
          115                      120                      125

Trp  Gln  Cys  Ser  Leu  Gln  Ser  Glu  Pro  Ser  Gly  His  Ile  Cys  Gly  Cys
     130                      135                      140

Val  Leu  Ile  Ala  Lys  Lys  Trp  Val  Leu  Thr  Val  Ala  His  Cys  Phe  Glu
145                      150                      155                           160

Gly  Arg  Glu  Asn  Ala  Ala  Val  Xaa  Lys  Val  Val  Leu  Gly  Ile  Asn  Asn
               165                      170                      175

Leu  Asp  His  Pro  Ser  Val  Phe  Met  Gln  Thr  Arg  Phe  Val  Lys  Thr  Ile
               180                      185                      190

Ile  Leu  His  Pro  Arg  Tyr  Ser  Arg  Ala  Val  Val  Asp  Tyr  Asp  Ile  Ser
          195                      200                      205

Ile  Val  Glu  Leu  Ser  Glu  Asp  Ile  Ser  Glu  Thr  Gly  Tyr  Val  Arg  Pro
     210                      215                      220

Val  Cys  Leu  Pro  Asn  Pro  Glu  Gln  Trp  Leu  Glu  Pro  Asp  Thr  Tyr  Cys
225                      230                      235                           240

Tyr  Ile  Thr  Gly  Trp  Gly  His  Met  Gly  Asn  Lys  Met  Pro  Phe  Lys  Leu
                    245                      250                      255

Gln  Glu  Gly  Glu  Val  Arg  Ile  Ile  Ser  Leu  Glu  His  Cys  Gln  Ser  Tyr
               260                      265                      270

Phe  Asp  Met  Lys  Thr  Ile  Thr  Thr  Arg  Met  Ile  Cys  Ala  Gly  Tyr  Glu
               275                      280                      285

Ser  Gly  Thr  Val  Asp  Ser  Cys  Met  Gly  Asp  Ser  Gly  Gly  Pro  Leu  Val
     290                      295                      300

Cys  Glu  Lys  Pro  Gly  Gly  Arg  Trp  Thr  Leu  Phe  Gly  Leu  Thr  Ser  Trp
305                      310                      315                           320

Gly  Ser  Val  Cys  Phe  Ser  Lys  Val  Leu  Gly  Pro  Gly  Val  Tyr  Ser  Asn
                325                      330                      335

Val  Ser  Tyr  Phe  Val  Glu  Trp  Ile  Lys  Arg  Gln  Ile  Tyr  Ile  Gln  Thr
               340                      345                      350

Phe  Leu  Leu  Asn
               355
```

( 2 ) INFORMATION FOR SEQ ID NO:2:

( i ) SEQUENCE CHARACTERISTICS:
        ( A ) LENGTH: 1739 base pairs
        ( B ) TYPE: nucleic acid
        ( C ) STRANDEDNESS: single
        ( D ) TOPOLOGY: linear ( i i ) MOLECULE TYPE: cDNA (vii) IMMEDIATE SOURCE:
    (A) LIBRARY: HEARNOT01
    (B) CLONE: 307474

(xi) SEQUENCE DESCRIPTION: SEQ ID NO:2:

| | | | | | |
|---|---|---|---|---|---|
| CCATCAGCTG | GGAGTCTTCT | CTTTTCCCTG | CACTTGTTCA | AACCAACTGT | TATAAATACC | 60 |
| TCATGTTCTT | TTCTTGCACC | ATTTTGGTAC | CAAAATGTGA | TGTGAATACA | GGCGAGCGTA | 120 |
| TCCCTCCTTG | CAGGGCATTG | TGTGAACACT | CTAAAGAACG | CTGTGAGTCT | GTTCTTGGGA | 180 |
| TTGTGGGCCT | ACAGTGGCCT | GAAGACACAG | ATTGCAGTCA | ATTTCCAGAG | GAAAATTCAG | 240 |
| ACAATCAAAC | CTGCCTGATG | CCTGATGAAT | ATGTGGAAGA | ATGCTCACCT | AGTCATTTCA | 300 |
| AGTGCCGCTC | AGGACAGTGT | GTTCTGGCTT | CCAGAAGATG | TGATGGCCAG | GCCGACTGTG | 360 |
| ACGATGACAG | TGATGAGGAA | AACTGTGGTT | GTAAAGAGAG | AGATCTTTGG | GAATGTCCAT | 420 |
| CCAATAAACA | ATGTTTGAAG | CACACAGTGA | TCTGCGATGG | GTTCCAGAC | TGCCCTGATT | 480 |
| ACATGGACGA | GAAAAACTGC | TCATTTTGCC | AAGATGATGA | GCTGGAATGT | GCAAACCATG | 540 |
| CGTGTGTGTC | ACGTGACCTG | TGGTGTGATG | GTGAAGCCGA | CTGCTCAGAC | AGTTCAGATG | 600 |
| AATGGGACTG | TGTGACCTCT | CTATAAATGT | GAACTCCTCT | TCCTTTCTGA | TGGTTCACAG | 660 |
| AGCTGCCACA | GAACACCATG | TGTGTGCAGA | TGGCTGGCAG | GAGATATTGA | GTCAGCTGGC | 720 |
| CTGCAAGCAG | ATGGGTTTAG | GAGAACCATC | TGTGACCAAA | TTGATACAGG | AACAGGAGAA | 780 |
| AGAGCCGCGG | TGGCTGACAT | TACACTCCAA | CTGGGAGAGC | CTCAATGGGA | CCACTTTACA | 840 |
| TGAACTTCTA | GTAAATGGGC | AGTCTTGTGA | GAGCAGAAGT | AAAATTTCTC | TTCTGTGTAC | 900 |
| TAAACAAGAC | TGTGGGCRCC | GCCCTGCTGC | CCGAATGAAC | AAAAGGATCC | TTGGAGGTCG | 960 |
| GACGAGTCGC | CCTGGAAGGT | GGCCATGGCA | GTGTTCTCTG | CAGAGTGAAC | CCAGTGGACA | 1020 |
| TATCTGTGGC | TGTGTCCTCA | TTGCCAAGAA | GTGGGTTCTG | ACAGTTGCCC | ACTGCTTCGA | 1080 |
| GGGGAGAGAG | AATGCTGCAG | TTYGGAAAGT | GGTGCTTGGC | ATCAACAATC | TAGACCATCC | 1140 |
| ATCAGTGTTC | ATGCAGACAC | GCTTTGTGAA | GACCATCATC | CTGCATCCCC | GCTACAGTCG | 1200 |
| AGCAGTGGTG | GACTATGACA | TCAGCATCGT | TGAGCTGAGT | GAAGACATCA | GTGAGACTGG | 1260 |
| CTACGTCCGG | CCTGTCTGCT | TGCCCAACCC | GGAGCAGTGG | CTAGAGCCTG | ACACGTACTG | 1320 |
| CTATATCACA | GGCTGGGGCC | ACATGGGCAA | TAAAATGCCA | TTTAAGCTGC | AAGAGGGAGA | 1380 |
| GGTCCGCATT | ATTTCTCTGG | AACATTGTCA | GTCCTACTTT | GACATGAAGA | CCATCACCAC | 1440 |
| TCGGATGATA | TGTGCTGGCT | ATGAGTCTGG | CACAGTTGAT | TCATGCATGG | GTGACAGCGG | 1500 |
| TGGGCCTCTT | GTTTGTGAGA | AGCCTGGAGG | ACGGTGGACA | TTATTTGGAT | TAACTTCATG | 1560 |
| GGGCTCCGTC | TGCTTTTCCA | AAGTCCTGGG | GCCTGGCGTT | TATAGTAATG | TGTCATATTT | 1620 |
| CGTCGAATGG | ATTAAAAGAC | AGATTTACAT | CCAGACCTTT | CTCCTAAACT | AATTATAAGG | 1680 |
| ATGATCAGAG | ACTTTTGCCA | GTACACTAAA | AGAAATGGCC | TTCTTGACTG | TGAGAGCTG | 1739 |

(2) INFORMATION FOR SEQ ID NO:3:

(i) SEQUENCE CHARACTERISTICS:
       (A) LENGTH: 638 amino acids
       (B) TYPE: amino acid
       (C) STRANDEDNESS: single
       (D) TOPOLOGY: linear (ii) MOLECULE TYPE: peptide (vii) IMMEDIATE SOURCE:
       (A) LIBRARY: GENBANK
       (B) CLONE: 205011

(xi) SEQUENCE DESCRIPTION: SEQ ID NO:3:

| | | | | | | | | | | | | | | |
|---|---|---|---|---|---|---|---|---|---|---|---|---|---|---|
| Met | Ile | Leu | Phe | Lys | Gln | Val | Gly | Tyr | Phe | Val | Ser | Leu | Phe | Ala | Thr |
| 1 | | | | 5 | | | | | 10 | | | | | 15 | |
| Val | Ser | Cys | Gly | Cys | Leu | Ser | Gln | Leu | Tyr | Ala | Asn | Thr | Phe | Phe | Arg |
| | | | 20 | | | | 25 | | | | | 30 | | | |
| Gly | Gly | Asp | Leu | Ala | Ala | Ile | Tyr | Thr | Pro | Asp | Ala | Gln | His | Cys | Gln |
| | | 35 | | | | | 40 | | | | 45 | | | | |
| Lys | Met | Cys | Thr | Phe | His | Pro | Arg | Cys | Leu | Leu | Phe | Ser | Phe | Leu | Ala |
| 50 | | | | | 55 | | | | | 60 | | | | | |
| Val | Ser | Pro | Thr | Lys | Glu | Thr | Asp | Lys | Arg | Phe | Gly | Cys | Phe | Met | Lys |
| 65 | | | | | 70 | | | | 75 | | | | | 80 | |
| Glu | Ser | Ile | Thr | Gly | Thr | Leu | Pro | Arg | Ile | His | Arg | Thr | Gly | Ala | Ile |
| | | | | 85 | | | | | 90 | | | | | 95 | |
| Ser | Gly | His | Ser | Leu | Lys | Gln | Cys | Gly | His | Gln | Leu | Ser | Ala | Cys | His |
| | | | 100 | | | | | 105 | | | | 110 | | | |
| Gln | Asp | Ile | Tyr | Glu | Gly | Leu | Asp | Met | Arg | Gly | Ser | Asn | Phe | Asn | Ile |
| | | | 115 | | | | | 120 | | | | 125 | | | |
| Ser | Lys | Thr | Asp | Ser | Ile | Glu | Glu | Cys | Gln | Lys | Leu | Cys | Thr | Asn | Asn |
| | 130 | | | | | 135 | | | | | 140 | | | | |
| Ile | His | Cys | Gln | Phe | Phe | Thr | Tyr | Ala | Thr | Lys | Ala | Phe | His | Arg | Pro |
| 145 | | | | | 150 | | | | | 155 | | | | | 160 |
| Glu | Tyr | Arg | Lys | Ser | Cys | Leu | Leu | Lys | Arg | Ser | Ser | Ser | Gly | Thr | Pro |
| | | | | 165 | | | | | 170 | | | | | 175 | |
| Thr | Ser | Ile | Lys | Pro | Val | Asp | Asn | Leu | Val | Ser | Gly | Phe | Ser | Leu | Lys |
| | | | 180 | | | | | 185 | | | | | 190 | | |
| Ser | Cys | Ala | Leu | Ser | Glu | Ile | Gly | Cys | Pro | Met | Asp | Ile | Phe | Gln | His |
| | | 195 | | | | | 200 | | | | | 205 | | | |
| Phe | Ala | Phe | Ala | Asp | Leu | Asn | Val | Ser | Gln | Val | Val | Thr | Pro | Asp | Ala |
| | 210 | | | | | 215 | | | | | 220 | | | | |
| Phe | Val | Cys | Arg | Thr | Val | Cys | Thr | Phe | His | Pro | Asn | Cys | Leu | Phe | Phe |
| 225 | | | | | 230 | | | | | 235 | | | | | 240 |
| Thr | Phe | Tyr | Thr | Asn | Glu | Trp | Glu | Thr | Glu | Ser | Gln | Arg | Asn | Val | Cys |
| | | | | 245 | | | | | 250 | | | | | 255 | |
| Phe | Leu | Lys | Thr | Ser | Lys | Ser | Gly | Arg | Pro | Ser | Pro | Pro | Ile | Ile | Gln |
| | | | 260 | | | | | 265 | | | | | 270 | | |
| Glu | Asn | Ala | Val | Ser | Gly | Tyr | Ser | Leu | Phe | Thr | Cys | Arg | Lys | Ala | Arg |
| | | 275 | | | | | 280 | | | | | 285 | | | |
| Pro | Glu | Pro | Cys | His | Phe | Lys | Ile | Tyr | Ser | Gly | Val | Ala | Phe | Glu | Gly |
| | 290 | | | | | 295 | | | | | 300 | | | | |
| Glu | Glu | Leu | Asn | Ala | Thr | Phe | Val | Gln | Gly | Ala | Asp | Ala | Cys | Gln | Glu |
| 305 | | | | | 310 | | | | | 315 | | | | | 320 |
| Thr | Cys | Thr | Lys | Thr | Ile | Arg | Cys | Gln | Phe | Phe | Thr | Tyr | Ser | Leu | Leu |
| | | | | 325 | | | | | 330 | | | | | 335 | |
| Pro | Gln | Asp | Cys | Lys | Ala | Glu | Gly | Cys | Lys | Cys | Ser | Leu | Arg | Leu | Ser |
| | | | 340 | | | | | 345 | | | | | 350 | | |
| Thr | Asp | Gly | Ser | Pro | Thr | Arg | Ile | Thr | Tyr | Glu | Ala | Gln | Gly | Ser | Ser |
| | | 355 | | | | | 360 | | | | | 365 | | | |
| Gly | Tyr | Ser | Leu | Arg | Leu | Cys | Lys | Val | Val | Glu | Ser | Ser | Asp | Cys | Thr |
| | 370 | | | | | 375 | | | | | 380 | | | | |
| Thr | Lys | Ile | Asn | Ala | Arg | Ile | Val | Gly | Gly | Thr | Asn | Ser | Ser | Leu | Gly |
| 385 | | | | | 390 | | | | | 395 | | | | | 400 |
| Glu | Trp | Pro | Trp | Gln | Val | Ser | Leu | Gln | Val | Lys | Leu | Val | Ser | Gln | Asn |
| | | | | 405 | | | | | 410 | | | | | 415 | |
| His | Met | Cys | Gly | Gly | Ser | Ile | Ile | Gly | Arg | Gln | Trp | Ile | Leu | Thr | Ala |

|     |     |     |     |     | 420 |     |     |     |     | 425 |     |     |     |     | 430 |     |     |
| --- | --- | --- | --- | --- | --- | --- | --- | --- | --- | --- | --- | --- | --- | --- | --- | --- | --- |
| Ala | His | Cys<br>435 | Phe | Asp | Gly | Ile | Pro<br>440 | Tyr | Pro | Asp | Val | Trp<br>445 | Arg | Ile | Tyr |
| Gly | Gly<br>450 | Ile | Leu | Asn | Leu | Ser<br>455 | Glu | Ile | Thr | Asn | Lys<br>460 | Thr | Pro | Phe | Ser |
| Ser<br>465 | Ile | Lys | Glu | Leu | Ile<br>470 | Ile | His | Gln | Lys | Tyr<br>475 | Lys | Met | Ser | Glu | Gly<br>480 |
| Ser | Tyr | Asp | Ile | Ala<br>485 | Leu | Ile | Lys | Leu | Gln<br>490 | Thr | Pro | Leu | Asn | Tyr<br>495 | Thr |
| Glu | Phe | Gln | Lys<br>500 | Pro | Ile | Cys | Leu | Pro<br>505 | Ser | Lys | Ala | Asp | Thr<br>510 | Asn | Thr |
| Ile | Tyr | Thr<br>515 | Asn | Cys | Trp | Val | Thr<br>520 | Gly | Trp | Gly | Tyr | Thr<br>525 | Lys | Glu | Arg |
| Gly | Glu<br>530 | Thr | Gln | Asn | Ile | Leu<br>535 | Gln | Lys | Ala | Thr | Ile<br>540 | Pro | Leu | Val | Pro |
| Asn<br>545 | Glu | Glu | Cys | Gln | Lys<br>550 | Lys | Tyr | Arg | Asp | Tyr<br>555 | Val | Ile | Thr | Lys | Gln<br>560 |
| Met | Ile | Cys | Ala | Gly<br>565 | Tyr | Lys | Glu | Gly | Gly<br>570 | Ile | Asp | Ala | Cys | Lys<br>575 | Gly |
| Asp | Ser | Gly | Gly<br>580 | Pro | Leu | Val | Cys | Lys<br>585 | His | Ser | Gly | Arg | Trp<br>590 | Gln | Leu |
| Val | Gly | Ile<br>595 | Thr | Ser | Trp | Gly | Glu<br>600 | Gly | Cys | Ala | Arg | Lys<br>605 | Glu | Gln | Pro |
| Gly | Val<br>610 | Tyr | Thr | Lys | Val<br>615 | Ala | Glu | Tyr | Ile | Asp<br>620 | Trp | Ile | Leu | Glu | Lys |
| Ile<br>625 | Gln | Ser | Ser | Lys | Glu<br>630 | Arg | Ala | Leu | Glu | Thr<br>635 | Ser | Pro | Ala |     |     |

(2) INFORMATION FOR SEQ ID NO:4:

(i) SEQUENCE CHARACTERISTICS:
  (A) LENGTH: 262 amino acids
  (B) TYPE: amino acid
  (C) STRANDEDNESS: single
  (D) TOPOLOGY: linear (ii) MOLECULE TYPE: peptide (iii) HYPOTHETICAL: NO (vii) IMMEDIATE SOURCE:
  (A) LIBRARY: GENBANK
  (B) CLONE: 125170

(xi) SEQUENCE DESCRIPTION: SEQ ID NO:4:

|     |     |     |     |     |     |     |     |     |     |     |     |     |     |     |     |
| --- | --- | --- | --- | --- | --- | --- | --- | --- | --- | --- | --- | --- | --- | --- | --- |
| Met<br>1 | Trp | Phe | Leu | Val<br>5 | Leu | Cys | Leu | Ala | Leu<br>10 | Ser | Leu | Gly | Gly | Thr<br>15 | Gly |
| Ala | Ala | Pro | Pro<br>20 | Ile | Gln | Ser | Arg | Ile<br>25 | Val | Gly | Gly | Trp | Glu<br>30 | Cys | Glu |
| Gln | His | Ser<br>35 | Gln | Pro | Trp | Gln | Ala<br>40 | Ala | Leu | Tyr | His | Phe<br>45 | Ser | Thr | Phe |
| Gln | Cys | Gly<br>50 | Gly | Ile | Leu | Val | His<br>55 | Arg | Gln | Trp | Val | Leu<br>60 | Thr | Ala | Ala |
| His<br>65 | Cys | Ile | Ser | Asp | Asn<br>70 | Tyr | Gln | Leu | Trp | Leu<br>75 | Gly | Arg | His | Asn | Leu<br>80 |
| Phe | Asp | Asp | Glu | Asn<br>85 | Thr | Ala | Gln | Phe | Val<br>90 | His | Val | Ser | Glu | Ser<br>95 | Phe |
| Pro | His | Pro | Gly<br>100 | Phe | Asn | Met | Ser | Leu<br>105 | Leu | Glu | Asn | His | Thr<br>110 | Arg | Gln |

-continued

| | | | | | | | | | | | | | | |
|---|---|---|---|---|---|---|---|---|---|---|---|---|---|---|
| Ala | Asp | Glu 115 | Asp | Tyr | Ser | His | Asp 120 | Leu | Met | Leu | Leu | Arg 125 | Leu | Thr | Glu |
| Pro | Ala 130 | Asp | Thr | Ile | Thr | Asp 135 | Ala | Val | Lys | Val | Val 140 | Glu | Leu | Pro | Thr |
| Gln 145 | Glu | Pro | Glu | Val | Gly 150 | Ser | Thr | Cys | Leu | Ala 155 | Ser | Gly | Trp | Gly | Ser 160 |
| Ile | Glu | Pro | Glu | Asn 165 | Phe | Ser | Phe | Pro | Asp 170 | Asp | Leu | Gln | Cys | Val 175 | Asp |
| Leu | Lys | Ile | Leu 180 | Pro | Asn | Asp | Glu | Cys 185 | Glu | Lys | Ala | His | Val 190 | Gln | Lys |
| Val | Thr | Asp 195 | Phe | Met | Leu | Cys | Val 200 | Gly | His | Leu | Glu | Gly 205 | Gly | Lys | Asp |
| Thr | Cys 210 | Val | Gly | Asp | Ser | Gly 215 | Gly | Pro | Leu | Met | Cys 220 | Asp | Gly | Val | Leu |
| Gln 225 | Gly | Val | Thr | Ser | Trp 230 | Gly | Tyr | Val | Pro | Cys 235 | Gly | Thr | Pro | Asn | Lys 240 |
| Pro | Ser | Val | Ala | Val 245 | Arg | Val | Leu | Ser | Tyr 250 | Val | Lys | Trp | Ile | Glu 255 | Asp |
| Thr | Ile | Ala | Glu 260 | Asn | Ser | | | | | | | | | | |